United States Patent
Koike et al.

(10) Patent No.: US 7,955,556 B2
(45) Date of Patent: Jun. 7, 2011

(54) ANALYZER

(75) Inventors: Hiroki Koike, Kobe (JP); Masayuki Ikeda, Kobe (JP)

(73) Assignee: Sysmex Corporation, Hyogo (JP)

( * ) Notice: Subject to any disclaimer, the term of this patent is extended or adjusted under 35 U.S.C. 154(b) by 380 days.

(21) Appl. No.: 11/062,933

(22) Filed: Feb. 23, 2005

(65) Prior Publication Data
US 2005/0186113 A1   Aug. 25, 2005

(30) Foreign Application Priority Data
Feb. 23, 2004   (JP) ................... 2004-045592

(51) Int. Cl.
*G01N 21/00* (2006.01)
(52) U.S. Cl. .......... 422/65; 422/63; 422/67; 422/82.01; 436/47; 436/48
(58) Field of Classification Search .......... 422/63, 422/65, 67, 82.01; 436/47, 48
See application file for complete search history.

(56) References Cited

U.S. PATENT DOCUMENTS

| | | | |
|---|---|---|---|
| 5,350,564 A * | 9/1994 | Mazza et al. ................. 422/63 |
| 5,588,555 A | 12/1996 | Kanamori et al. | |
| 5,876,670 A * | 3/1999 | Mitsumaki et al. ............ 422/65 |
| 6,074,617 A * | 6/2000 | DeYoung et al. ............. 422/104 |
| 6,331,437 B1 | 12/2001 | Cohen et al. | |
| 6,444,171 B1 * | 9/2002 | Sakazume et al. ............. 422/65 |
| 6,588,625 B2 * | 7/2003 | Luoma et al. .................. 221/9 |
| 6,735,531 B2 * | 5/2004 | Rhett et al. .................... 702/31 |
| 2002/0015665 A1 * | 2/2002 | Lindsey et al. ................ 422/64 |
| 2002/0021983 A1 * | 2/2002 | Comte et al. ................... 422/65 |
| 2002/0031444 A1 * | 3/2002 | Ito et al. ......................... 422/62 |
| 2003/0070498 A1 * | 4/2003 | Ohyama et al. ............ 73/863.01 |
| 2003/0213313 A1 * | 11/2003 | Katagi ....................... 73/864.25 |
| 2005/0074361 A1 | 4/2005 | Tanoshima et al. | |

FOREIGN PATENT DOCUMENTS

| | | | |
|---|---|---|---|
| JP | 54159288 A | * | 12/1979 |
| JP | 04-169337 | | 6/1992 |
| JP | 2001-153872 A | | 6/2001 |

* cited by examiner

*Primary Examiner* — Jyoti Nagpaul
(74) *Attorney, Agent, or Firm* — Sughrue Mion, PLLC

(57) ABSTRACT

An analyzer capable of operating in a normal processing mode performing sequential analysis of a plurality of specimens and in an interrupting mode performing analysis of an urgent specimen that comprising a suction unit for suctioning an urgent specimen, an analysis unit for analyzing an urgent specimen suctioned by the suction unit, an urgent specimen container holder for holding an urgent specimen container containing an urgent specimen, and a moving mechanism for moving the urgent specimen container holder between a placement position at which an urgent specimen container is placed in the holder, and a suction position at which an urgent specimen is suctioned from an urgent specimen container, wherein the moving mechanism comprises a movement force supplying mechanism for supplying a force to move the urgent specimen container holder from the suction position to the placement position is disclosed.

6 Claims, 14 Drawing Sheets

ANALYZER

FIELD OF THE INVENTION

The present invention relates to an analyzer, and specifically relates to an analyzer capable of operating in a normal processing mode performing sequential analysis of a plurality of specimens and in an interrupting mode performing analysis of an urgent specimen.

BACKGROUND

Conventional analyzers are known which are capable of operating in a normal processing mode performing sequential analysis of a plurality of specimens and in an interrupting mode performing analysis of an urgent specimen (for example, Japanese Laid-Open Patent Publication No. 2001-153872).

Japanese Laid-Open Patent Publication No. 2001-153872 discloses a automated urine analyzer constructed such that an urgent specimen container holder is movable between an urgent specimen container placement position and dispensing position.

In this automated urine analyzer, since the user must manually move the urgent specimen container holder from the dispensing position to the placement position to assay the urgent specimen, a problem arises in that the operation of placing the urgent specimen container is complicated. Specifically, the operation is not simple since the operation is performed while the urgent specimen container is held in the hand.

In this automated urine analyzer, there is a possibility that the specimen suction nozzle may be damaged when the user moves the urgent specimen container holder while the specimen suction nozzle, which is used for suctioning the urgent specimen, is inserted in the urgent specimen container.

Furthermore, this automated urine analyzer does not take into consideration that an assay of an urgent specimen may be started when an urgent specimen container has not been placed in the urgent specimen container holder, and under this circumstance the automated urine analyzer performs a wasteful operation since an urgent specimen cannot be suctioned.

SUMMARY

The scope of the present invention is defined solely by the appended claims, and is not affected to any degree by the statements within this summary.

An object of the present invention is to provide an analyzer having improved usability.

A first aspect of the present invention is an analyzer capable of operating in a normal processing mode performing sequential analysis of a plurality of specimens and in an interrupting mode performing analysis of an urgent specimen, comprising: a suction unit for suctioning an urgent specimen; an analysis unit for analyzing an urgent specimen suctioned by the suction unit; an urgent specimen container holder for holding an urgent specimen container containing an urgent specimen; and a moving mechanism for moving the urgent specimen container holder between a placement position at which an urgent specimen container is placed in the holder, and a suction position at which an urgent specimen is suctioned from an urgent specimen container; wherein the moving mechanism comprises a movement force supplying mechanism for supplying a force to move the urgent specimen container holder from the suction position to the placement position.

A second aspect of the present invention is an analyzer capable of operating in a normal processing mode performing sequential analysis of a plurality of specimens and in an interrupting mode performing analysis of an urgent specimen, comprising: a transport mechanism for transporting a specimen container containing a specimen, the transport mechanism operating in the normal processing mode; an urgent specimen container holder for holding an urgent specimen container containing an urgent specimen; a suction unit for suctioning a specimen transported by the transport mechanism in the normal processing mode and an urgent specimen in the interrupting mode; an analysis unit for analyzing a specimen and an urgent specimen suctioned by the suction unit; a sensor for detecting an urgent specimen container held in the urgent specimen container holder; and an interrupting mode start means for starting the interrupting mode after the sensor detecting an urgent specimen container.

A third aspect of the present invention is an analyzer capable of operating in a normal processing mode performing sequential analysis of a plurality of specimens and in an interrupting mode performing analysis of an urgent specimen, comprising: a suction unit for suctioning an urgent specimen; an analysis unit for analyzing an urgent specimen suctioned by the suction unit; an urgent specimen container holder for holding an urgent specimen container containing an urgent specimen; a moving mechanism for moving the urgent specimen container holder between a suction position at which an urgent specimen is suctioned from an urgent specimen container, and another position; a locking mechanism for preventing the movement of the urgent specimen container holder from the suction position to another position; and a lock control means for controlling the locking mechanism such that at least while an urgent specimen is being suctioned by the suction unit, the urgent specimen container holder is unable to move from the suction position to another position.

DETAILED DESCRIPTION OF THE PREFERRED EMBODIMENT

The preferred embodiment of the present invention is described hereinafter with reference to the drawings.

The general structure of an embodiment of the analyzing system is described hereinafter with reference to FIGS. 1 and 2. The analyzing system 100 is capable of operating in a normal processing mode performing sequential analysis of a plurality of specimens and in an interrupting mode performing analysis of an urgent specimen. The interrupting mode may interrupt the normal processing mode when an urgent specimen is required to be analyzed while normal processing mode is executing.

Figure 1:
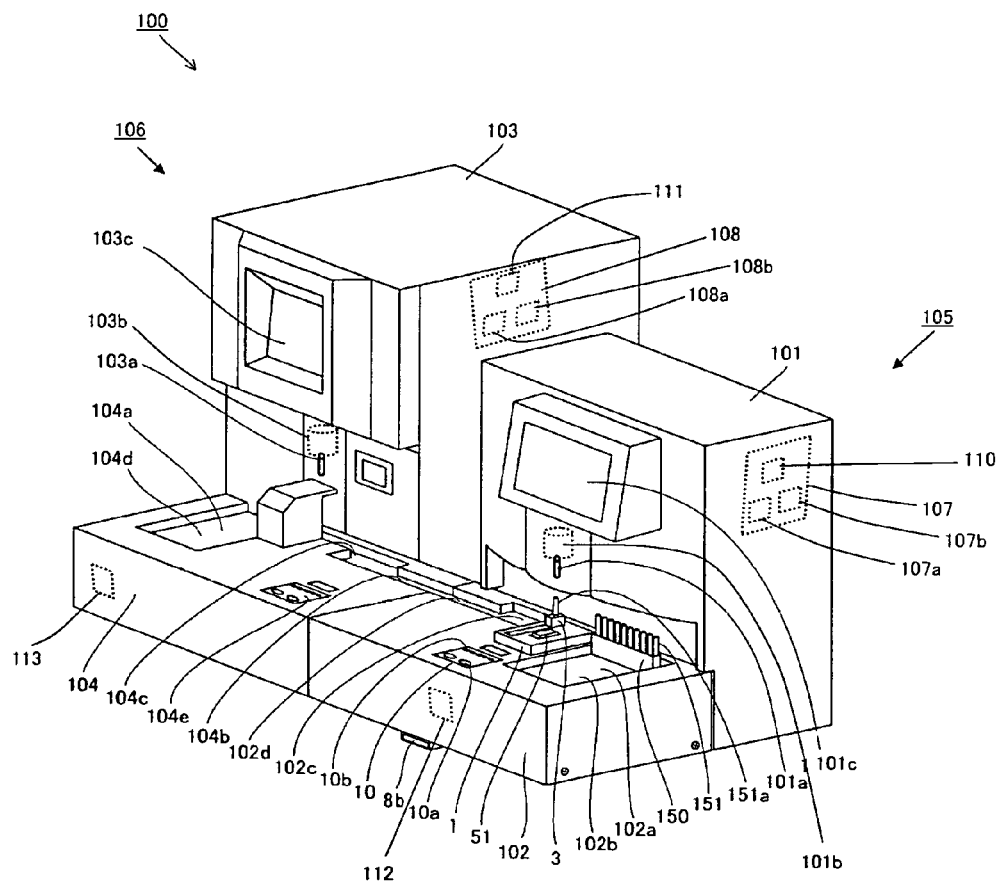
FIG. 1 is a perspective view showing the general structure of an analyzing system including a first analyzer and first transport device of an embodiment of the present invention.
Figure 2:
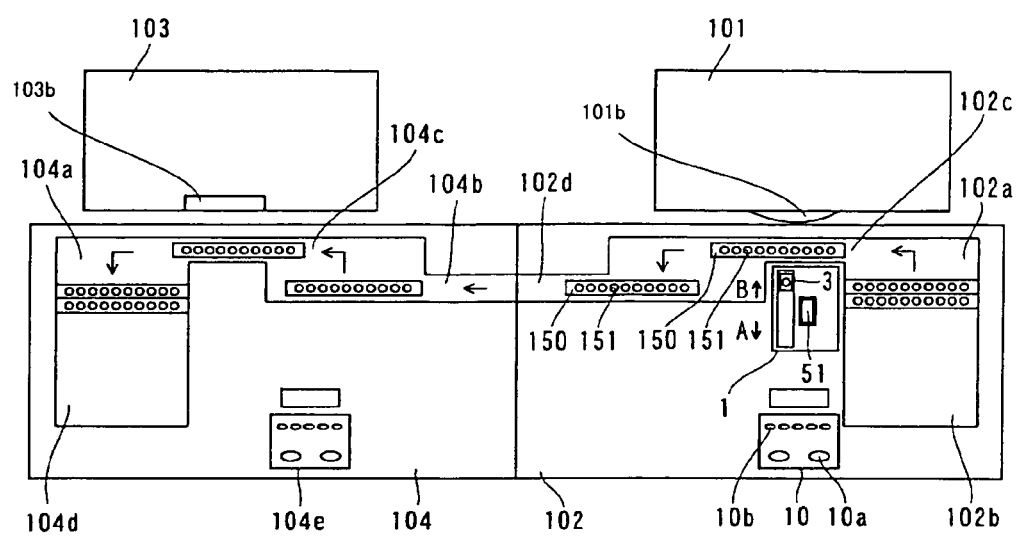
FIG. 2 briefly illustrates the operation of the analyzing system of FIG. 1.

As shown in FIG. 1, the analyzing system 100 of the present embodiment is provided with a first analyzer 105 which includes a first analyzer body 101 and first transport device 102, and a second analyzer 106 which includes a second analyzer body 103 and second transport device 104. The first analyzer 105 and second analyzer 106 are urine analyzers. The second analyzer 106 is connected to the latter section of the first analyzer 105, so as to analyze the urinalysis result of the first analyzer 105 in greater detail. The first transport device 102 transports the specimen container so as to automatically supply a specimen to the first analyzer body 101, and the second transport device 104 transports a specimen container so as to automatically supply a specimen to the second analyzer body 103.

The first analyzer body 101 is provided with a suction unit 101b which includes a specimen suction nozzle 101a capable of moving in forward-and-back directions and vertical directions, analysis unit 107 for analyzing a specimen (urine) suctioned by the suction unit 101b, and a display unit 101c. The second analyzer body 103 is provided with a suction unit 103b which includes a specimen suction nozzle 103a capable of moving in vertical directions, analysis unit 108 for analyzing a specimen (urine) suctioned by the suction unit 103b, and a display unit 103c.

The analysis unit 107 is provided with a sample dispensing unit 107a which has the function of dispensing a specimen suctioned by the suction unit 101b onto a test paper, detection unit 107b for detecting optical information from the specimen dispensed onto the test paper by the sample dispensing unit 107a, and a controller 110 for calculating analysis result of the specimen (qualitative result of the urine) from the optical information detected by the detection unit 107b.

The controller 110 has the further function of controlling the suction unit 101b and display unit 101c and the like.

The analysis unit 108 is provided with a sample preparation unit 108a which has the function of preparing a specimen suctioned by the suction unit 103b and introducing the prepared sample into a flow cell (not shown in the drawing), detection unit 108b for detecting optical information from the specimen introduced into the flow cell by the sample preparation unit 108a, and a controller 111 for calculating an analysis result from the optical information detected by the detection unit 108b.

The controller 111 has the further function of controlling the suction unit 103b and display unit 103c and the like. The controllers 110 and 111 are provided with microcomputers which include a CPU, ROM, RAM and the like.

The first transport device 102 includes a transport mechanism 102a for transporting a specimen rack 150 which holds a plurality (ten tubes in the present embodiment) of specimen containers (test tubes) containing specimen. The transport mechanism 102a includes a forwarding unit 102b, transverse feeding unit 102c, and discharge unit 102d.

The first transport unit 102 is provided with a touch panel-type liquid crystal display 10 for performing operation settings and displaying setting values and messages and the like. A start button 10a used for starting the normal processing mode is displayed on the display 10. Also displayed on the display 10 with a predetermined timing is a start button 10b for starting the interrupting mode.

The first transport device 102 is provided with a controller 112. The controller 112 is provided with a microcomputer including a CPU, ROM, RAM and the like, and has the capability of communicating with the controller 110 and a controller 113 described later. The controller 112 has the function of controlling the transport mechanism 102a, and a locking mechanism 6 described later.

The second transport device 104 includes a transport mechanism 104a for transporting a specimen rack 150 which holds a plurality of specimen containers 151 containing specimens. The transport mechanism 104a is formed by a forwarding unit 104b, transverse feeding unit 104c, and collection unit 104d. Furthermore, a setting unit 104e is provided for performing operation setting for the second transport device 104. The second transport device 104 is further provided with a controller 113. The controller 113 is provided with a microcomputer which includes a CPU, ROM, RAM and the like, and is capable of communicating with the controllers 111 and 112. The controller 113 has the function of controlling the transport mechanism 104a and the like.

The first transport device 102 is provided with an urgent specimen supply unit 1 which is used when the analyzer 100 operates in the interrupting mode.

The urgent specimen supply unit 1 is provided on the front side (arrow A side in FIG. 3) forward from the position at which a specimen is suctioned from the specimen container 151 by the suction unit 10b to facilitate placement of the specimen container.

In the present embodiment, an urgent specimen is a specimen has a higher priority than a specimen contained in a container 151 held by the specimen rack 150 and require a urgent analysis result.

A specimen container 151 is transported by the transport mechanism 102a and assayed automatically, whereas an urgent specimen container is placed in the urgent specimen supply unit 1 by a user, and assayed while the transport of the specimen container 151 is suspended by an operation performed through the display 10.

Figure 3:
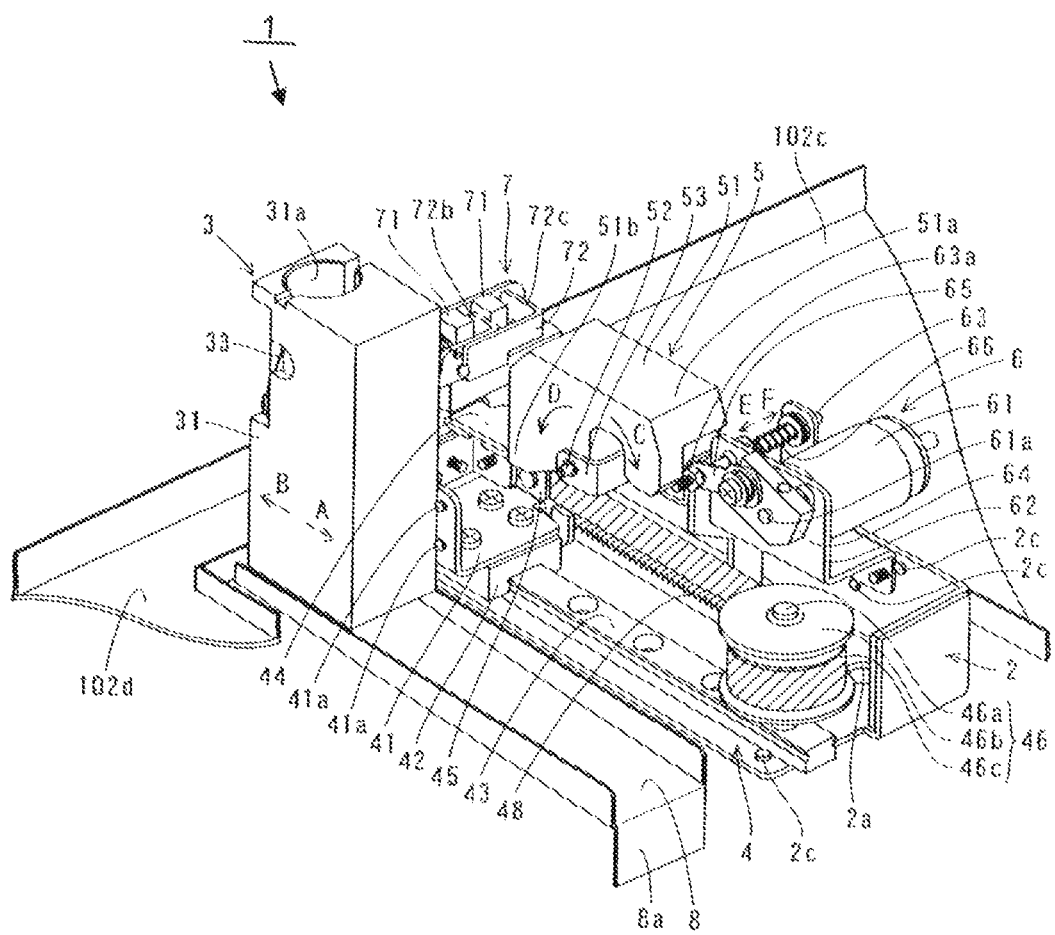
FIG. 3 is a perspective view showing the structure of the periphery of the urgent specimen supply unit of the first transport device of the embodiment of FIG. 1.

The structure of the urgent specimen supply unit 1 is described in detail below with reference to FIGS. 1 through 7. The urgent specimen supply unit 1 briefly includes a frame 2, urgent specimen container holder 3, moving mechanism 4, push button mechanism 5, locking mechanism 6, sensor 7, and tray 8, as shown in FIG. 3.

Figure 4:
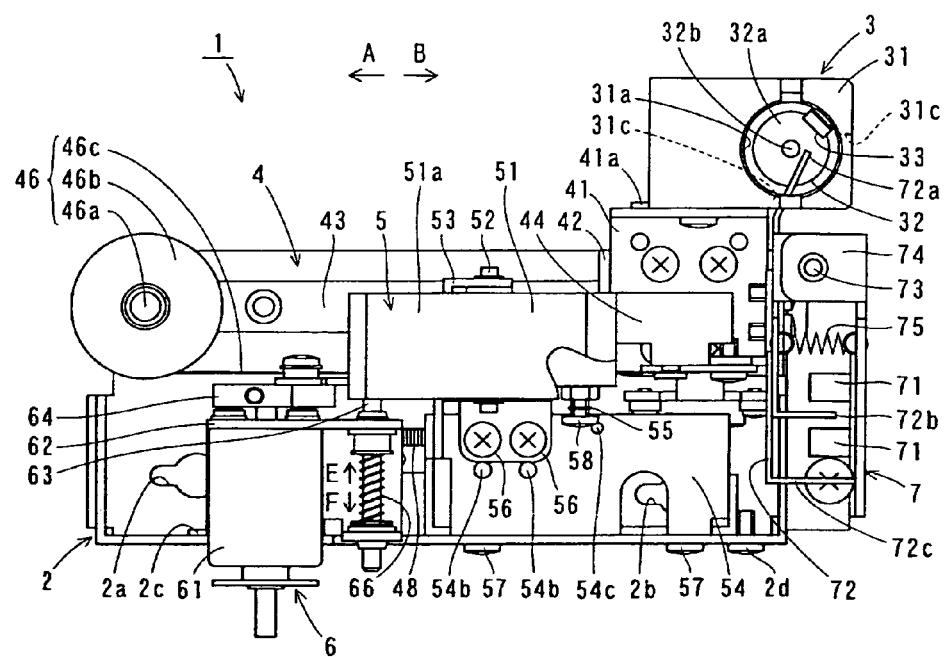
FIG. 4 is a top view of the urgent specimen supply unit of the first transport device of the embodiment of FIG. 3.
Figure 5:
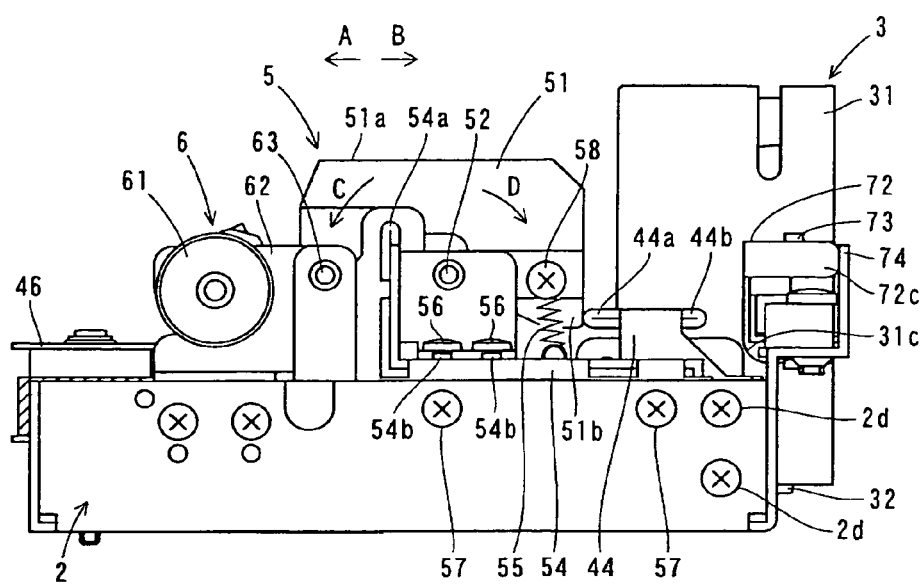
FIG. 5 is a front view of the urgent specimen supply unit of the first transport device of the embodiment of FIG. 4.

Formed on the frame 2 are screw holes 2a and 2b for attaching the urgent specimen supply unit 1 to the device body of the first transport device 102, as shown in FIG. 4. The screw holes 2a and 2b include a large diameter part which has a diameter greater than the diameter of the head of the screw (not shown in the drawing), and a screw slot part which has a width smaller than the diameter of the screw head and connected to the large diameter part. Consequently, when attaching the urgent specimen supply unit 1 to the device body, the urgent specimen supply unit 1 is raised from a low position with the screws attached beforehand to the device body, and after the screws are inserted into the large diameter part of the screw holes 2a and 2b, the screws are positioned at the screw slot parts of the screw holes 2a and 2b by sliding the urgent specimen supply unit in a horizontal direction. Then, the urgent specimen supply unit 1 is fixedly attached to the device by tightening the screws at the screw slot parts. Furthermore, a plurality of positioning convexities 2c are provided on the inside surface of the frame 2, as shown in FIG. 3. Two positioning screws 2d are mounted so as to project from the inside surface of the frame 2, as shown in FIGS. 4 and 5.

Figure 7:
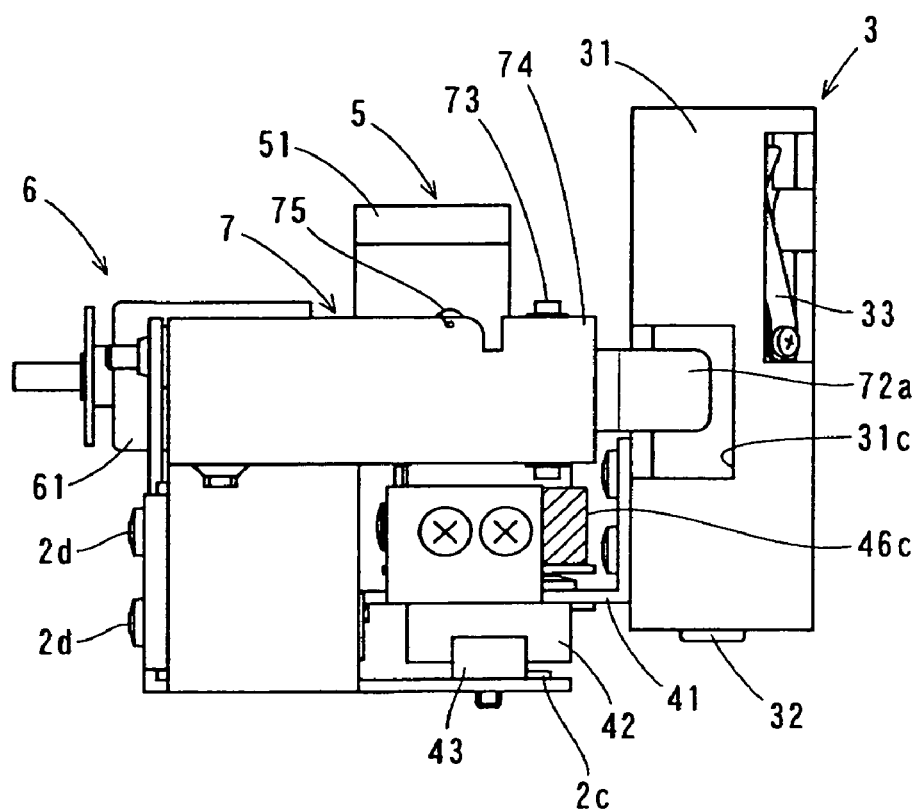
FIG. 7 is a right side view of the urgent specimen supply unit of the first transport device of the embodiment of FIG. 5.

As shown in FIG. 4, the urgent specimen container holder 3 includes a specimen container holding member 31 formed of resin, a bottom receiver 32 formed of rubber, and a flat spring 33. The specimen container holding member 31 has a specimen container receiving hole 31a for detachably accommodating a test tube-like urgent specimen container 151a. The bottom receiver 32, which is formed of rubber, is arranged at the bottom of the specimen container receiving hole 31a, and has the function of supporting the bottom of the urgent specimen container 151a. The bottom receiver 32 is also provided with a tapered (becoming narrow at one end) receiving surface 32a, and a hole 32b for discharging a specimen that spills from the urgent specimen container 151a. The flat spring 33 is arranged so as to protrude at the inner surface of the specimen container receiving hole 31a of the specimen container holding member 31. The flat spring 33 has the function of holding the urgent specimen container 151a accommodated within the specimen container receiving hole 31a by pressing against it with a predetermined pressing force. Consequently, it is possible accommodate various urgent specimen containers 151a having different diameters since urgent specimen containers 151a having different diameters (for example, 14 to 16 mm) can be held safely without instability. The specimen container holding member 31 is further provided with a notch 31c capable of accommodating a contact 72a of a detector 72 described later, as shown in FIGS. 4 and 7. The notch 31c is provided so as to not touch the contact 72a of the detector 72 at any location when an urgent specimen container 151a is not placed in the specimen container holding member 31, and so as to touch the contact 72a on the side surface of the urgent specimen container 151a when an urgent specimen container 151a is placed in the specimen container holding member 31.

The moving mechanism 4 includes a mounting plate 41, a direct-drive guide formed by a slider 42 and slide rail 42, push button connector 44, spring mount 45, constant load spring (spiral coil spring) 46, pinion 47, and rack 48. The specimen container holding member 31 of the urgent specimen container holder 3 is mounted on the slider 42 through the mounting plate 41. A positioning convexity 41a is provided at the mounting position of the urgent specimen container holder 3 on the mounting plate 41. Consequently, it is possible to mount the specimen container holder 31 at a precise position relative to the slider 42 frame 2). The slider 42 is mounted on the slide rail 43 so as to be slidable in the forward-and-back directions (arrow A and arrow B directions). The slide rail 43 is mounted on the bottom surface of the frame 2. Consequently, the urgent specimen container holder 3 is constructed so as to be movable in forward-and-back directions (arrow A and arrow B directions) between the suction position (position shown in FIG. 3) and the placement position of the urgent specimen container 151a (position shown in FIG. 9). The push button connector 44 is provided with one end 44a which is connectable with a connector 51b on the rear bottom surface of a push button 51 described later, and another end 44b which slides in contact with the bottom surface of the push button 51 when the urgent specimen container holder 3 moves from the placement position to the suction position. The one end 44a and other end 44b of the push button connector 44 are formed in a rounded shape by means of a fold-back process (hemming) so as to prevent damage to the resin push button 51. The spring mount 45 is mounted on the mounting plate 41 through the push button connector 44.

Figure 6:
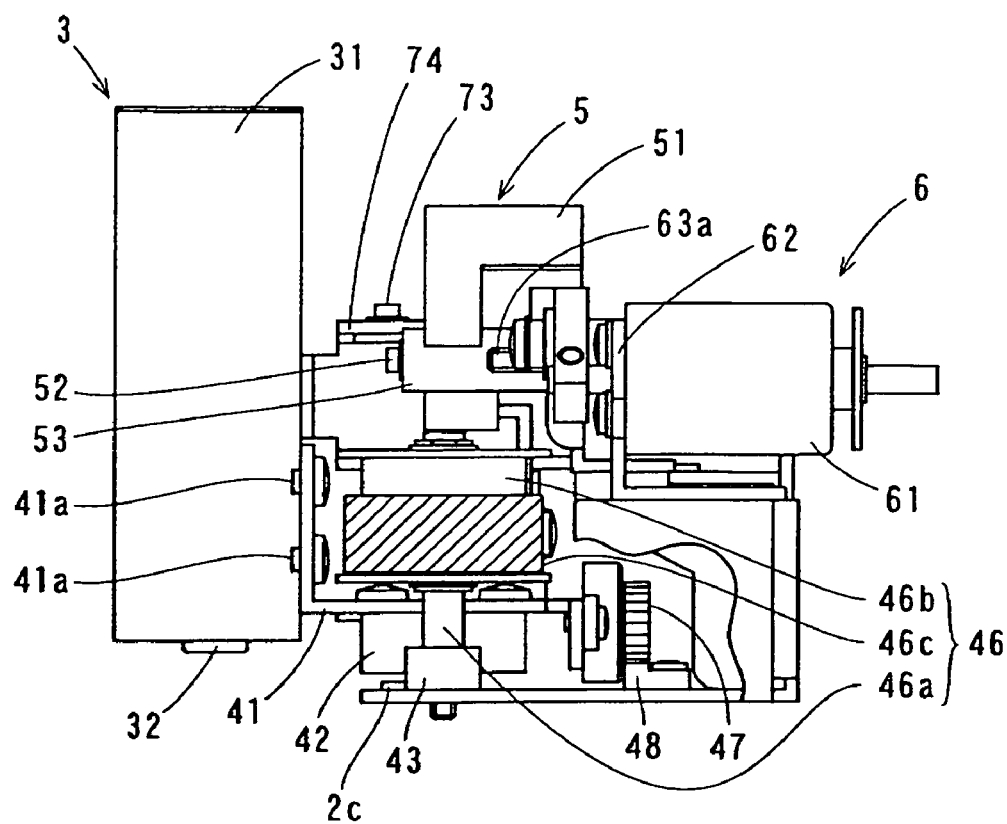
FIG. 6 is a left side view of the urgent specimen supply unit of the first transport device of the embodiment of FIG. 5.

The constant load spring 46 is formed by a metal shaft 46a, resin drum 46b mounted on the shaft 46a so as to be rotatable, and a flat metal spring 46c wrapped around the drum 46b, as shown in FIGS. 3, 4, and 6. The constant load spring 46 has the function of exerting a constant force on the urgent specimen container holder 3. A threaded part is provided on the tip of the shaft 46a of the constant load spring 46, as shown in FIG. 6, and this threaded part is attached to the bottom surface of the frame 2 so as to anchor the slide rail 43. The slider 42 is prevented from detaching from the front of the slide rail 43 (arrow A direction in FIG. 3) by means of the shaft 46a of the constant load spring 46. The tip of the spring 46c of the constant load spring 46 is fixedly attached to the spring mount 45 which is mounted on the mounting plate 41 through the push button connector 44.

As shown in FIG. 6, the pinion 74 is mounted on the mounting plate 41, and the rotating part is oiled. The rack 48 is mounted on the bottom of the frame 2 so as to be movable in forward-and-back directions (arrow A and arrow B directions) while the pinion 47 is engaged, as shown in FIGS. 3 and 6. The pinion 47 and rack 48 have the function of attenuating the speed at which the urgent specimen container holder 3 moves from the suction position to the placement position by the constant load spring 46.

The push button mechanism 51 is a switch for starting the move of the urgent specimen container holder 3 from the suction position to the placement position. As shown in FIGS. 3 through 5, the push button mechanism 5 includes a push button 51 formed of resin, a metal support shaft 52 for supporting the push button 51 so as to be rotatable, a metal support shaft support member 53 for supporting the support shaft 52, a metal support plate 54 for mounting the support shaft support member 53, and a tension coil spring 55 for exerting a force so as to rotate the push button 51 in the arrow D direction. The push button 51 is arranged on the right side of the urgent specimen container holder 3 when viewed from the user's side (refer to FIGS. 1 and 2), so as to be convenient for right-handed users. The push button 51 is provided with a pressing part 51a, and a connector 51b to connect to the push button connector 44. A support plate 54 is integratedly provided with a regulating member 54a for regulating the amount of rotation of the push button 51 in the forward and downward direction (arrow C direction), positioning convexity 54b, and spring mounting hole 54c, as shown in FIGS. 4 and 5. The regulating member 54a contacts the front bottom surface of the push button 51. As shown in FIG. 5, the tip of the regulating member 54a is rounded by a fold-back process (hemming process) so as to prevent damage to the resin push button 51. As shown in FIG. 4, the support shaft holding member 53 is mounted on the top surface of the support plate 54 by screws 56 using the positioning concavity 54b as reference. The support plate 54 is mounted on the inner side of the frame 2 using the two positioning screws 2d mounted on the frame 2 as references. Consequently, it is possible to precisely mount the support plate 54 and support shaft holding member 53 on the frame 2. On end of the tension coil spring 55 is attached to the push button 51 by a mounting screw 58, and the other end of the tension coil spring 55 is attached to the support plate 54 by a spring mounting screw 54c.

As shown in FIGS. 3 and 4, the locking mechanism 6 includes a solenoid valve 61, bracket 62 for mounting the solenoid valve 61, lock shaft 63 mounted on the bracket 62 so as to be movable in the arrow E and arrow F directions, resin link member 64 mounted on a shaft 61a of the solenoid valve 61, metal link member 65 for connecting the link member 64 and lock shaft 63, and compression coil spring 66 for exerting a force at the lock release position on the tip 63a of the lock shaft 63.

By linking the connecting parts of the link member 64 and link member 65 through the two lining members 64 and 65, the total link distance of the link members 64 and 65 can be automatically adjusted to the distance between the shaft 61a of the solenoid valve 61 and the lock shaft 63 by moving the connecting part of the link member 64 and the link member 65 in vertical directions even when the design measurements of the link members 64 and 65 are slightly divergent. Consequently, it is possible to absorb any divergence in the measurements of the link members 64 and 65.

As shown in FIGS. 3 and 4, the sensor 7 includes a light transmitting-type optical sensor 71, detection piece 72, support shaft 73 for supporting the detection piece 72 so as to be rotatable, mounting plate 74 integratedly formed with the frame 72 for mounting the support shaft 73 and optical sensor 71, and a tension coil spring 75 for exerting a force to rotate the detection piece 72 to the optical sensor 71 side. The detection piece 72 is provided with a contact 72a which contacts the urgent specimen container 151a accommodated in the urgent specimen container holder 3, a shield 72b for shielding the light transmitting part of the optical sensor 71, and a mounting plate contact 72c for regulating the origin position of the detection piece 72 by contacting the inner surface of the mounting plate 74. The optical sensor 71 is OFF when the shield 72b of the detection piece 72 blocks the light transmitting part of the optical sensor 71, and is ON when the light transmitting part is not blocked.

The tray 8 is provided below the urgent specimen container holder 3 to receive any urgent specimen that spilled from the urgent specimen container 151a. The tray 8 is inclined so as to be lower toward the front (arrow A direction in FIG. 3). The leading edge of the tray 8 is provided with a tongue 8a for directing the specimen spilled in the tray downward. A removable bottom tray (not shown in the drawing) is provided below the tongue 8a of the tray 8. Consequently, damage to the device is prevented even when specimen is spilled by providing the tray 8 and the bottom tray.

The operation of the analyzing system of the present embodiment is described below. First, the specimen rack 150 which accommodates a plurality of specimen containers 151 containing specimens (urine) is automatically transported in the arrow direction in the normal processing mode, as shown in FIG. 2. Specifically, a user first places the specimen rack 150, which accommodates a plurality of specimen containers 151 containing specimens, in the transport unit 102b of the first transport device 102. Then, the user presses the start button 10a displayed on the display 10. Consequently, The analyzing system 100 starts the normal processing mode, and the specimen rack 150 placed in the transport unit 102b of the first transport device 102 is transported to the transverse feeding unit 102c. Next, the specimen containers 151 are sequentially transported one container at a time to a position opposite the specimen suction nozzle 101a when the specimen rack 150 is transversely fed by the transverse feeding unit 102c. After the specimen suction nozzle 101a is moved to the front, it is lowered and the suctioning operation is performed, then the nozzle is lifted and moved backward to sequentially suction specimen contained in the specimen containers 151 transported to the position opposite the specimen suction nozzle 101a. Thereafter, the specimen rack 150 is transported from the transverse feeding unit 102c to the discharge unit 102d, and subsequently transported to the forwarding unit 104b of the second transport device 104. The second transport device 104 detects the presence of the specimen rack 150 transported to the forwarding unit 104b, and starts operating.

The specimen rack 150, which has been transported to the forwarding unit 104b of the second transport device 104, is transported to the transverse feeding unit 104c of the second transport device 104. then, the specimen containers 151 are sequentially transported one at a time to a position opposite the specimen suction nozzle 103a by transverse feeding of the specimen rack 150 by the transverse feeding unit 104c. The second analyzer body 103 suctions and analyzes only the specimens determined to require detailed urinalysis (quantitative assay of components in the urine) by the second analyzer body 103 based on the urinalysis result of the first analyzer body 101. Thereafter, the specimen rack 150 is transported from the transverse feeding unit 104c to the collection unit 104d. The operations described above are performed sequentially for each specimen rack 150.

Figure 8:
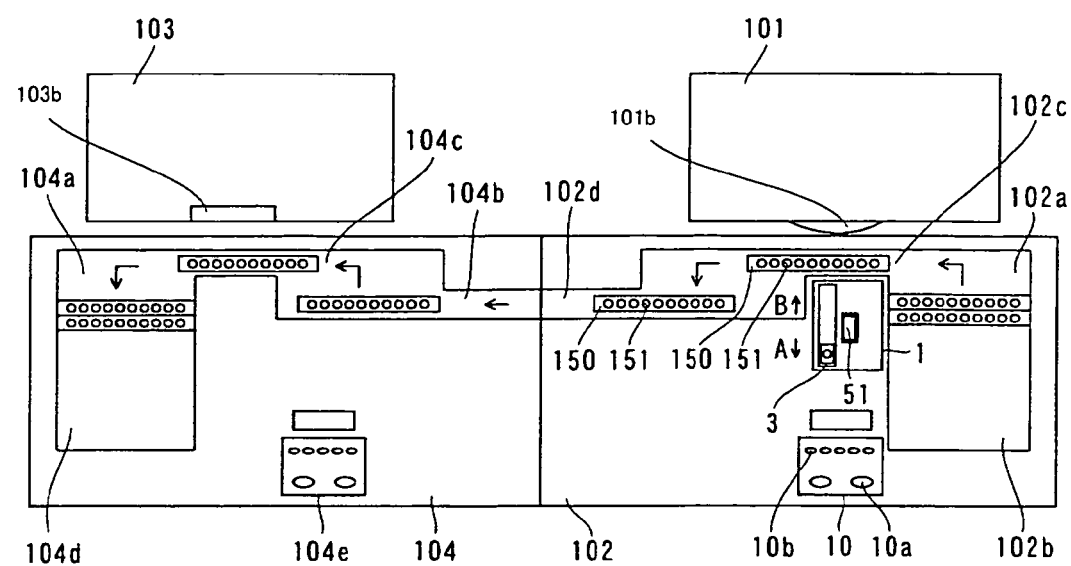
FIG. 8 briefly illustrates the operation of the analyzing system of FIG. 1.
Figure 9:
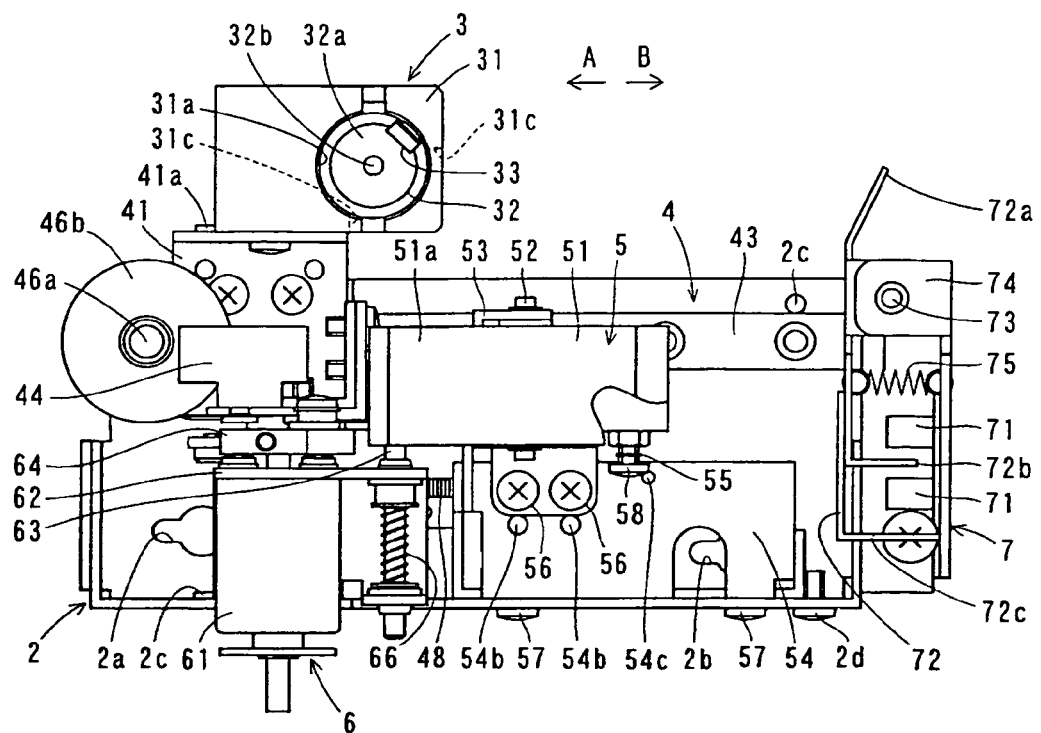
FIG. 9 is a top view showing the condition of the urgent specimen container holder moved to the placement position in the embodiment of FIG. 5.

Operations before starting the interrupting mode is described below. In the initial state, the urgent specimen container holder 3 is at the initial position, that is, the suction position, as shown in FIGS. 2 through 4. Since the urgent specimen container holder 3 does not hold any urgent specimen containers 151a in the initial state, the shield 72b of the detection piece 72 is positioned so as to block the light transmitting part of the optical sensor 71. Accordingly, the optical sensor 71 is OFF. From this state, the push button 51 is rotated in the arrow C direction by pressing the pressing part 51a of the push button 51, as shown in FIG. 3. Consequently, the engagement of the push button 51 and the push button connector 44 is released because the connector 51b rear bottom surface of the push button 51 is raised. Therefore, the slider 42 is moved in the arrow A direction by the force exerted by the spring 46c of the constant load spring 46 mounted on the push button connector 44 through the spring mount 45. The urgent specimen container holder 3 is also moved to the placement position of the urgent specimen containers 151a in conjunction with the movement of the slider 42 in the arrow A direction. Consequently, the state shown in FIGS. 8 and 9 is achieved.

Figure 10:
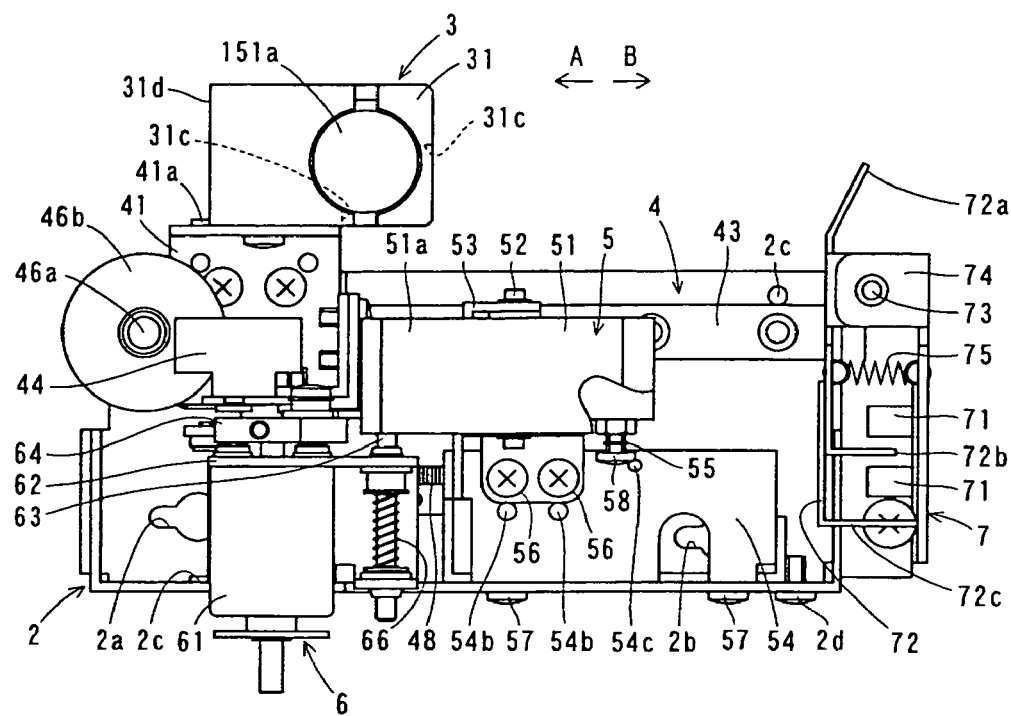
FIG. 10 is a top view showing the condition of the urgent specimen container placed in the urgent specimen container holder when the urgent specimen container holder has been moved to the placement position shown in FIG. 9.
Figure 11:
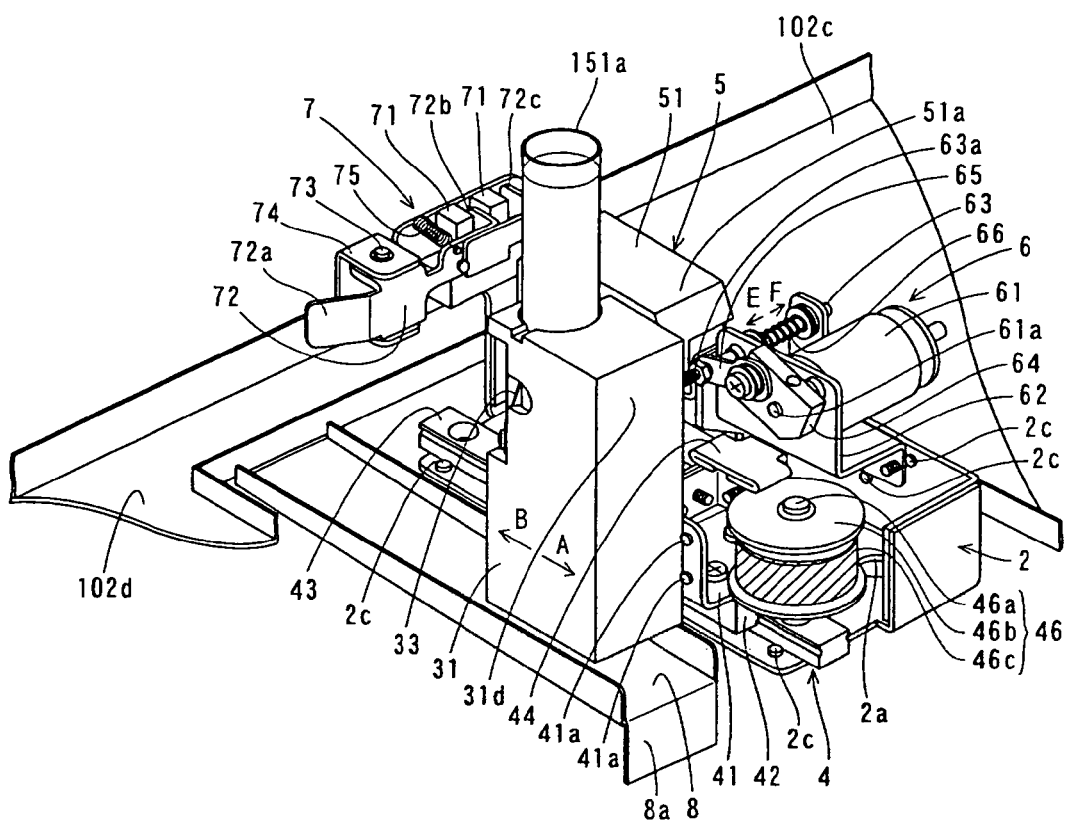
FIG. 11 is a perspective view of the urgent specimen container placed in the urgent specimen container holder shown in FIG. 10.
Figure 12:
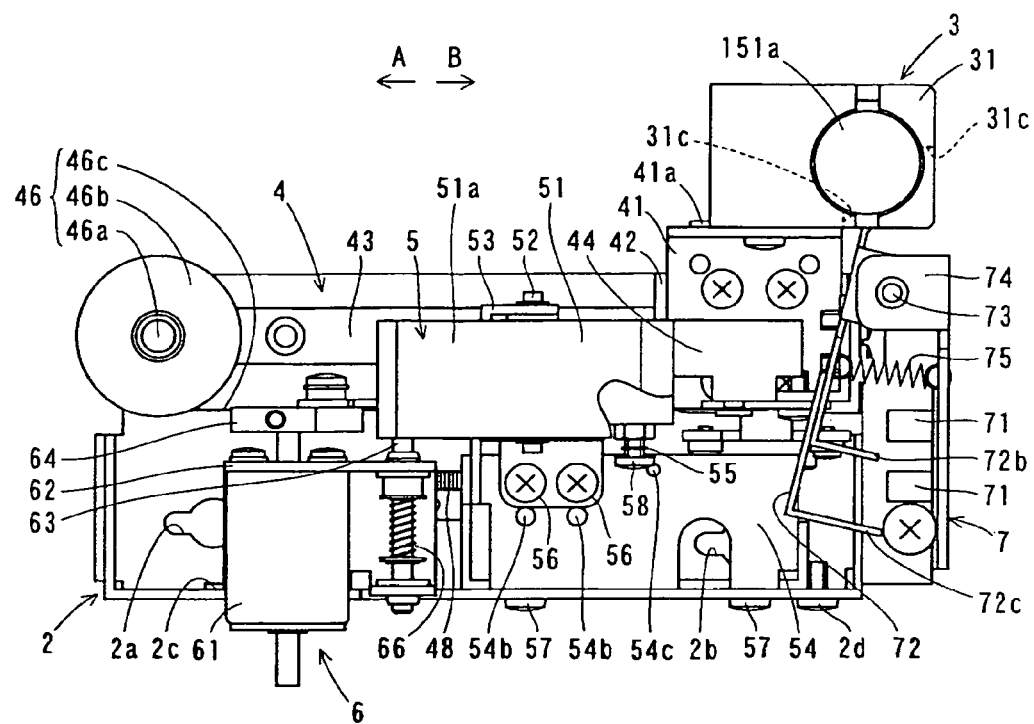
FIG. 12 is a top view of the urgent specimen container holder moved to the suction position with the urgent specimen container placed in the urgent specimen container holder in an embodiment of the present invention.

When the urgent specimen container holder 3 is at the placement position (shown in FIGS. 8 and 9), the user places the urgent specimen containers 151a containing the urgent specimen in the urgent specimen container holder 3. Consequently, the condition shown in FIGS. 10 and 11 is achieved. From this state, the specimen container holding member 31 is moved to the suction position (position in FIG. 3) by pressing the back surface 31d of the specimen container holding member 31 in the arrow B direction. In this case, the specimen container holding member 31 is moved in the arrow B direction against the force exerted by the constant load spring 46, and the push button connector 44 slides along the bottom surface of the push button 51 and engages the connector 51b of the rear bottom surface of the push button 51. Consequently, the specimen container holding member 31 is anchored at the suction position. Furthermore, when the specimen container holding member 31 accommodates an urgent specimen container 151a and reaches the suction position, the shield 72b is moved to a position at which the shield 72b does not block the light transmitting part of the optical sensor 71 when the contact 72a is pressed by the back surface of the urgent specimen container 151a accommodated in the urgent specimen container holder 3, such that the detection piece 72 is rotated. Consequently, the optical sensor 71 is ON.

Figure 14:
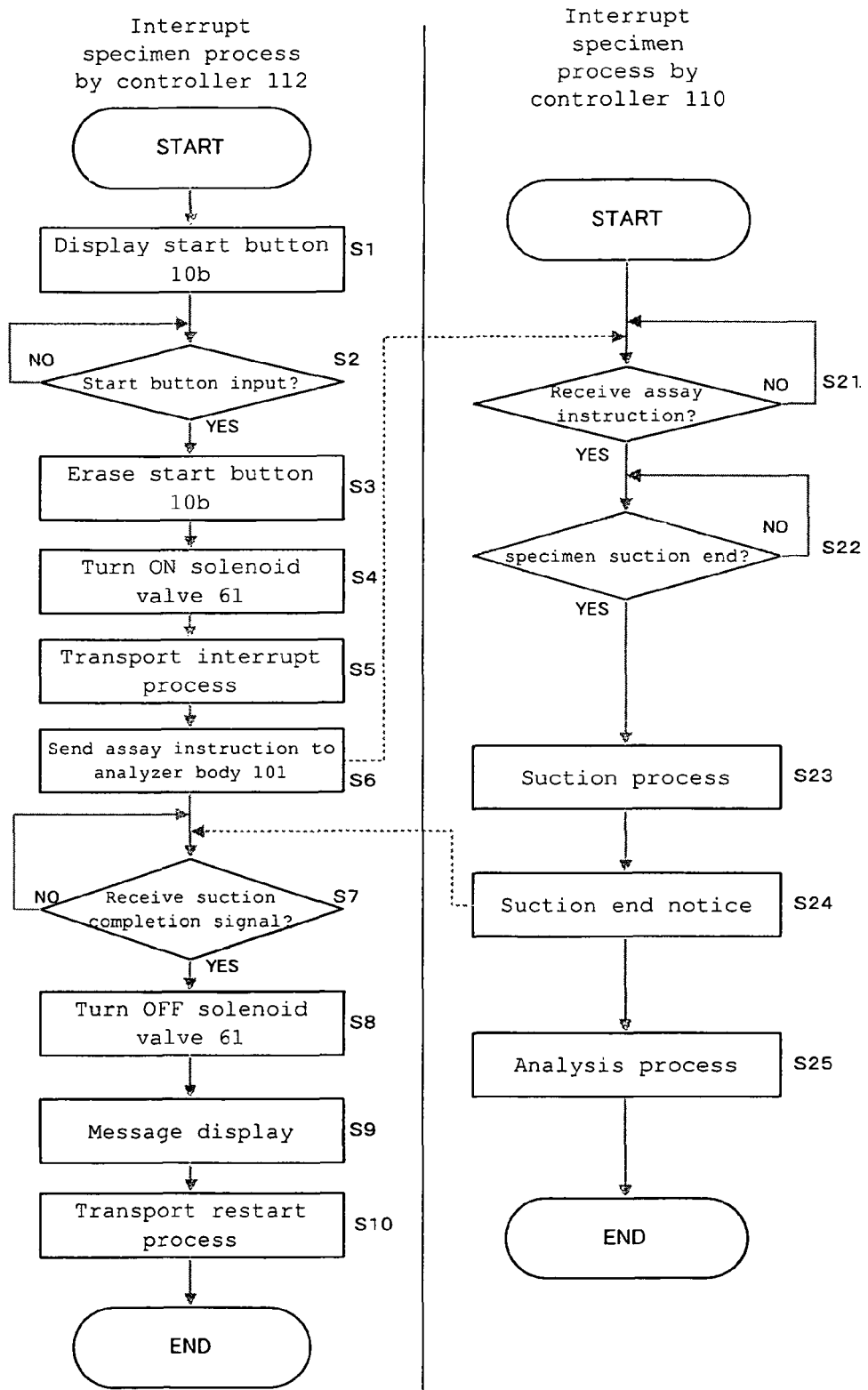
FIG. 14 is a flow chart illustrating the sequence of the interrupt specimen process of an embodiment of the analyzer of the present invention.

When the optical sensor 71 is turned ON, the controllers 110 and 112 start the interrupt specimen process. The interrupt specimen process is described below with reference to FIG. 14. The interrupt specimen process are processes executed in parallel with the transport process of the specimen rack 150 by the controller 112, and the assay process of the specimen contained in specimen container 151 by the controller 110 and the like.

In step S1, the controller 112 executes a process to display the start button 10b for starting an analysis of urgent specimen on the display 10. Consequently, a reception of analysis instruction is permitted.

In step S2, the controller 112 waits that the start button 10b is input.

When the start button 10b is input (step S2: YES), the interrupting mode starts and the controller 112 executes a process to erase the start button 10b from the display 10 in step S3.

Figure 13:
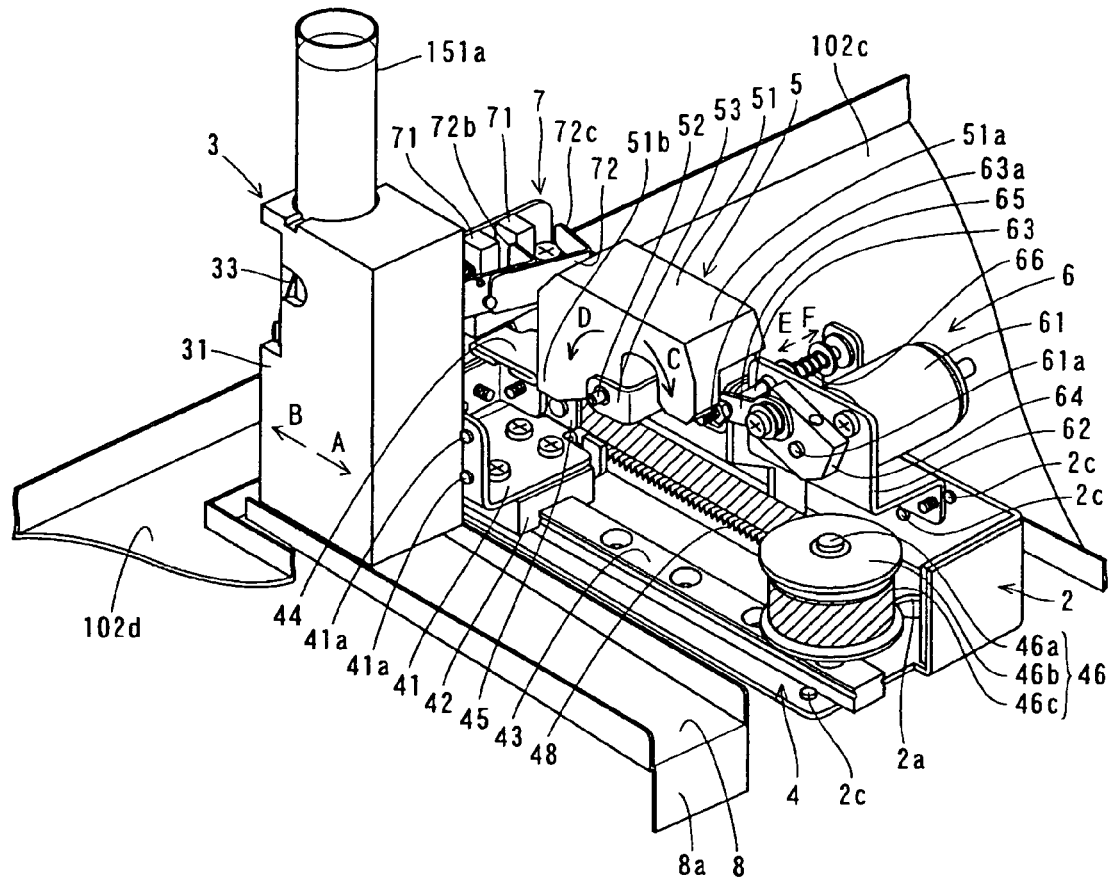
FIG. 13 is a perspective view of the urgent specimen container holder moved to the suction position shown in FIG. 12.

In step S4, the controller 112 executes a process to turn ON the solenoid valve 61. Consequently, the solenoid valve 61 is turned ON, and the shaft 61a of the solenoid valve 61 is moved in the arrow E direction (refer to FIG. 13). Accordingly, the tip 63a of the lock shaft 63 is moved to the lock position against the force exerted by the compression coil spring 66, such that the push button 51 becomes locked and unable to rotate in the arrow C direction by the tip 63a of the lock shaft 63. Consequently, the push button 51 enters an inoperative state, and the urgent specimen container holder 3 cannot be moved from the suction position to the placement position before the suction unit 10b starts the suction operation of the urgent specimen.

In step S5, the controller 112 executes a process to interrupt the transport of the specimen rack 150. This transport interrupt process executes a process in which a specimen rack 150 currently being transported is stopped after transported to a predetermined position (for example, a specimen rack 150 being transported by the transverse feeding unit 102b is stopped at the position of transverse feeding of one specimen container 151), and the stopped specimen rack 150 is maintained in the stopped state.

In step S6, the controller 112 sends a signal to the controller 110 of the first analyzer body 101 which specifies that an urgent specimen assay is to be performed.

In step S21, the controller 110 waits to receive the signal from the controller 112.

When the signal is received from the controller 112 (step S21: YES), then in step S22, the controller 110 waits until the suction operation for the specimen contained in the specimen container 151 positioned opposite the specimen suction nozzle 101a has been completed.

When the specimen suction operation ends (step S22: YES), then in step S23, the controller 110 executes a process to suction the urgent specimen, that is, executes a process to move the specimen suction nozzle 101a forward and downward, suction the urgent specimen from the urgent specimen container 151a, and move the specimen suction nozzle 101a upward and backward.

When the process of step S23 ends, then in step S24, the controller 110 sends a signal indicating that the suction operation is completed to the controller 112.

Then, in step S25, the controller 110 executes a process for analyzing the specimen in the analysis unit 107.

In step S7, the controller 112 waits to receive the signal indicating that the suction operation is completed from the controller 110.

When the signal is received from the controller 110 (step S7: YES), then in step S8, the controller 112 executes a process to turn OFF the solenoid valve 61. Consequently, the solenoid valve 61 is turned OFF, and the tip 63a of the lock shaft 63 and the shaft 61a of the solenoid valve 61 return in the arrow F direction by means of the force exerted by the spring 66. As a result, the tip 63a of the lock shaft 63 is moved to the lock release position such that the lock on the push button 51 is released. Consequently, the push button 51 becomes operational, and the urgent specimen container holder 3 becomes movable from the suction position to the placement position.

In step S9, the controller 112 executes a process for displaying on the display 10 a message indicating that the urgent specimen container holder 3 is now movable from the suction position to the placement position. This message is automatically erased from the display 10 5 minutes after the message is first displayed. Furthermore, this message is erased from the display 10 before 5 minutes has elapsed from the time the message is first displayed, when the optical sensor 71 is turned OFF.

In step S10, the controller 112 executes a process to restart the transport of the specimen rack 150. Thereby, the interrupting mode ends and returns to the normal processing mode.

As described above, when the optical sensor 71 is turned ON, that is, when the urgent specimen container holder 3 is at the suction position and the urgent specimen container 151a is placed in the urgent specimen container holder 3, the start button 10b is displayed on the display 10, and it is possible to start the urgent specimen assay.

Furthermore, when suctioning of the urgent specimen is completed by the suction unit 101b as described above, the first transport device 102 automatically restarts the transport operation of the specimen rack 150.

The processes performed by the user after the interrupt specimen process ends are described below.

After lock on the push button 51 is released, the urgent specimen container holder 3 is automatically moved in the arrow A direction to the placement position for the urgent specimen container 151a when the user presses the push button 51. Specifically, the push button 51 is first rotated in the arrow C direction when the user presses the pressing part 51a of the push button 51. Consequently, the connector 51b on the rear bottom of the push button 51 is raised, and the engagement of the push button 51 and the push button connector 44 is released. Therefore, the slider 42 is moved in the arrow A direction by the force exerted by the spring 46c of the constant load spring 46 mounted on the push button 46 through the spring mount 45. The urgent specimen container holder 3 is also moved in the arrow A direction to the urgent specimen container 151a placement position in conjunction with the movement of the slider 42 in the arrow A direction. Thereafter, the user removes the assayed urgent specimen container 151a. Then, when another urgent specimen assay is required, the urgent specimen assay is performed by repeating the operations described above.

In the present embodiment described above, there is a low probability of the user's hand actually touching the specimen suction nozzle because the urgent specimen container holder 3 can be returned from the suction position to the placement position without the user touching the urgent specimen container holder 3 situated at the suction position of the specimen suction nozzle since the constant load spring 46 is provided to supply a force to move the urgent specimen container holder 3 from the suction position to the placement position.

Furthermore, since the urgent specimen container holder 3 is automatically moved to the placement position, the operation of placing the urgent specimen container 151a is simple even when the urgent specimen container 151a is held in the user's hand.

In the present embodiment, the constant load spring 46 supplies a force to move the urgent specimen container holder 3 from the suction position to the placement position more inexpensively than when using a motor.

In the present embodiment, since the constant load spring 46 is used to move the urgent specimen container holder 3 with a constant force, the speed of the urgent specimen container holder 3 does not rapidly change during the movement, thereby preventing spillage of the specimen during the movement of the urgent specimen container holder 3. Furthermore, in the present embodiment, spillage of the specimen during the movement of the urgent specimen container holder can be more accurately prevented because the constant load spring 46 moves the urgent specimen container holder 3 at low speed from the suction position to the placement position due to the provision of the rack 48 and pinion 47 which engages the rack 48.

In the present embodiment, a push button 51 is provided to start the movement of the urgent specimen container holder 3 from the suction position to the placement position, such that the movement of the urgent specimen container holder 3 from the suction position to the placement position can be easily started simply by the user pressing the push button 51.

In the present embodiment, the locking mechanism 6 is provided for rendering the push button 51 non-operational during the suctioning of the urgent specimen by the specimen suction nozzle, thereby preventing movement of the urgent specimen container holder 3 from the suction position to the placement position during suction of the urgent specimen by the specimen suction nozzle.

The embodiment disclosed above has been described by way of examples in all aspects and is not to be considered as restrictive in any sense. The scope of the present invention is expressed by the scope of the claims and not by the description of the embodiment. The present invention may be variously modified insofar as such modification is within the scope and equivalences of the claims.

For example, although a constant load spring (biasing mechanism) is used as a movement force supplying mechanism, the invention is not limited to such mechanism inasmuch as biasing mechanisms other than a constant load spring also may be used. Drive sources such as a motor and the like also may be used as the movement force supplying mechanism.

When a motor is used as the movement force supplying mechanism, the specimen container holder may be moved from the suction position to the placement position when the user presses a switch to start the operation of the motor, or the motor may be automatically started to move the specimen container holder from the suction position to the placement position after the specimen suctioning has ended.

Although the urgent specimen container holder is constructed so as to move in straight line from the suction position to the placement position in the embodiment, the present invention is not limited to this construction inasmuch as the movement may be a curve. For example, the urgent specimen container holder may be placed on the outer periphery of a disk-shaped table which is rotated by means of a drive source such as a motor or the like to move the urgent specimen container holder from the suction position to the placement position.

The present embodiment is constructed so that the specimen contained in the specimen container 151 and urgent specimen are suctioned by a single specimen suction nozzle in the present embodiment, however, the present invention is not limited to this construction inasmuch as separate nozzles may be provided for suctioning specimen contained in the specimen container 151 and suctioning urgent specimens.

Although the present embodiment is designed so as to display a start button 10b when the urgent specimen container holder 3 is at the suction position and an urgent specimen container 151a is placed in the urgent specimen container holder 3, the present invention is not limited to this arrangement inasmuch as the start button 10b also may be displayed when an urgent specimen container is placed in the urgent specimen container holder fixed at a predetermined position.

The urgent specimen container holder 3 is locked immediately after there is input from the start button 10b in the present embodiment, however the invention is not limited to this arrangement since the urgent specimen container holder 3 also may be locked after a predetermined time has elapsed since input from the start button 10b insofar as the lock occurs before the specimen suction nozzle has been inserted into the urgent specimen container 151a to suction an urgent specimen.

Although the start button 10b is displayed on the display 10 when the optical sensor 71 is turned ON in the above embodiment, the present invention is not limited to this arrangement inasmuch as the start button 10b may be normally displayed on the display 10 beforehand, such that the start button 10b is rendered ineffective when the optical sensor 71 is turned OFF, and the start button 10b is rendered effective when the optical sensor 71 is turned ON. Furthermore, a mechanical switch may be used as the start button 10b, such that the start button 10b is rendered ineffective when the optical sensor 71 is turned OFF, and the start button 10b is rendered effective when the optical sensor 71 is turned ON.

In the present embodiment, the controllers 110 and 112 communicate and the interrupt specimen process is executed, however, the present invention is not limited to this arrangement, and the interrupt specimen process may be executed by either one or the other of the controller 110 and controller 112.

Although a mechanical push button is used as the movement starting means in the above embodiment, the present invention is not limited to this usage, inasmuch as an electrical switch for starting a supply of current to a motor also may be used as the movement starting means when a motor is used as the movement force supplying mechanism for moving the urgent specimen container holder. In this case, the locking mechanism 4 also may lock the urgent specimen container holder by render the electrical switch non-operative.

The above embodiment is capable of accommodating test tube-like urgent specimen containers in the urgent specimen container holder, however, the present invention is not limited to this mode inasmuch as the specimen container holder may be constructed so as to accommodate a urine collection cup.

The present invention has been described by way of example in which a first analyzer body and first transport device are connected in the above embodiment, however, the present invention is not limited to this arrangement, and the invention is also applicable to apparatuses in which the analyzer and transport device are integratedly incorporated.

In the above described embodiment, the present invention is applied to an analyzer which includes a urine analyzer and a transport device, however, the present invention is not limited to this mode, since, for example, the invention is also applicable to analyzers which include, for example, a transport device and a blood analyzer body or the like.

The present invention has been described by way of example in which the invention is applied to an analysis system which includes two analyzers, however, the present invention is not limited to this mode inasmuch as the invention also may be applied to single analyzers and analysis systems which include three or more analyzers.

What is claimed is:

1. An analyzer capable of operating in a normal processing mode performing sequential analysis of a plurality of non-urgent specimens and in an interrupting mode performing analysis of an urgent specimen, comprising:
   means for transporting a non-urgent specimen container containing a non-urgent specimen to a first suction position at which a non-urgent specimen is suctioned, the means for transporting operating in the normal processing mode;
   means for holding an urgent specimen container containing an urgent specimen at a second suction position at which an urgent specimen is suctioned, wherein the second suction position is located out of a route on which non-urgent specimen containers are transported by the means for transporting;
   a slide rail for guiding a movement of the means for holding between a placement position at which an urgent specimen is placed in the means for holding and the second suction position;
   a locking mechanism for locking the means for holding at the second suction position to prevent a movement of the means for holding from the second suction position toward the placement position;
   a suction nozzle for suctioning a non-urgent specimen transported by the means for transporting at the first suction position in the normal processing mode and an urgent specimen at the second suction position in the interrupting mode;
   means for analyzing a non-urgent specimen and an urgent specimen suctioned by the suction nozzle; and
   a controller for performing operations in a following order, the operations comprising:
      locking the means for holding at the second suction position by the locking mechanism, wherein an urgent specimen container is held in the means for holding and the means for holding has been moved from the placement position to the second suction position;
      interrupting the transport of a non-urgent specimen container by the means for transporting;
      suctioning an urgent specimen in the urgent specimen container by the suction nozzle; and
      releasing the locking mechanism of the means for holding.

2. The analyzer of claim 1, wherein non-urgent specimens analyzed in the normal processing mode and an urgent specimen analyzed in the interrupting mode are urine, and the means for analyzing analyzes urine suctioned by the nozzle.

3. The analyzer of claim 1, further comprising:
   a sensor for detecting an urgent specimen container at the second suction position held in the means for holding; and
   a display for displaying a start button for starting an analysis of an urgent specimen,
   wherein the controller controls the display to display the start button according to detection by the sensor before locking of the means for holding.

4. The analyzer of claim 3, wherein the controller controls the display to erase the start button from the display according to input of the start button.

5. The analyzer of claim 3, wherein the controller interrupts the transport of the non-urgent specimen container by the means for transporting according to input of the start button.

6. The analyzer of claim 3, wherein the controller controls the means for transporting to automatically restart the transport of the non-urgent specimen container after releasing the locking mechanism of the means for holding.

* * * * *